(12) United States Patent
Paxson et al.

(10) Patent No.: US 11,766,499 B2
(45) Date of Patent: Sep. 26, 2023

(54) ODOR REDUCING DEVICE

(71) Applicant: Doskocil Manufacturing Company, Inc., Arlington, TX (US)

(72) Inventors: Ryan Paxson, Elk Rapids, MI (US); Michael Harper, Fort Worth, TX (US)

(73) Assignee: DOSKOCIL MANUFACTURING COMPANY, INC., Arlington, TX (US)

( * ) Notice: Subject to any disclaimer, the term of this patent is extended or adjusted under 35 U.S.C. 154(b) by 0 days.

(21) Appl. No.: 17/182,546

(22) Filed: Feb. 23, 2021

(65) Prior Publication Data

US 2021/0260239 A1      Aug. 26, 2021

Related U.S. Application Data

(60) Provisional application No. 62/981,174, filed on Feb. 25, 2020.

(51) Int. Cl.
*A61L 9/12* (2006.01)

(52) U.S. Cl.
CPC .......... *A61L 9/12* (2013.01); *A61L 2209/133* (2013.01); *A61L 2209/15* (2013.01)

(58) Field of Classification Search
None
See application file for complete search history.

(56) References Cited

U.S. PATENT DOCUMENTS

| | | | | |
|---|---|---|---|---|
| 4,168,551 A | * | 9/1979 | Hautmann | E03D 9/032 4/223 |
| 4,261,957 A | * | 4/1981 | Schimanski | E03D 9/032 248/213.2 |
| 4,301,556 A | * | 11/1981 | Schimanski | E03D 9/032 4/231 |
| RE32,017 E | * | 11/1985 | Hautmann | B01F 21/22 4/231 |
| 4,777,670 A | * | 10/1988 | Klinkhammer | B01F 21/22 4/231 |
| 5,460,787 A | * | 10/1995 | Colon | A61L 9/12 239/55 |
| 2005/0148479 A1 | * | 7/2005 | Barthel | D06F 58/30 510/101 |
| 2007/0245470 A1 | * | 10/2007 | Nguyen | E03D 9/032 4/223 |
| 2011/0138526 A1 | * | 6/2011 | Hsu | E03D 9/03 4/223 |

(Continued)

OTHER PUBLICATIONS

Amazon.com. Mainetti 5131 Clear Plastic Hangers w. 360 Swivel Metal Hook & Sturdy Metal Non-Slip Padded Clips. [online] [retri. on Oct. 20, 2021], p. 1. https://www.amazon.com/Mainetti-Plastic-Hangers-Non-Slip-Bottoms/dp/B07JMYCKM2/ref=sr_1_11?dchild=1&keywords=rotating%2Bhanger%2Bclear&qid=1634768069&qsid=144-5769818-2328239&sr=8-11&sres=B01M13TXC7%2CB07JMNVF1Y%2CB07TMLKP3W%2CB08LYLZ289%2CB07MH3DBCT%2CB085TD9JHV%2CB00MJZYXKC%2CB01EENC9VQ%2CB07JMYCKM2%2CB017N2T4ZO%2CB0027IS7D0%2CB08SKWWCW9%2CB07MSKN3DK%2CB07RQCSSJ7%2CB01IRHUV6A%2CB08B5ZL82K%2CB005W9V5BM%2CB01J7T4686%2CB01N9570W4%2CB0000TQF2S&srpt=CLOTHES_HANGER&th=1 (Year: 2018).*

(Continued)

*Primary Examiner* — Jelitza M Perez

(74) *Attorney, Agent, or Firm* — GLOBAL IP COUNSELORS, LLP

(57) ABSTRACT

An odor reducing device for a cat litterbox includes a housing and a fastener. The housing has a front sidewall and a rear sidewall. The front and rear sidewalls together defines a top opening that opens to an interior of the housing. The fastener is attached to the housing and is configured to support the housing on the litterbox.

12 Claims, 16 Drawing Sheets

(56) References Cited

U.S. PATENT DOCUMENTS

2014/0076991 A1* 3/2014 Irwin .................. A61L 2/00
4/228.1

OTHER PUBLICATIONS

Menards.com—Arm & Hammer Clean Burst Odor Busterz Closet Mate 2pack [online][retr.Apr. 27, 2022],pp.1-3. https://www.menards.com/main/storage-organization/closet-organizers/closet-organizers-accessories/arm-hammer-trade-clean-burst-trade-odor-busterz-trade-closet-mate-2-pack/48286/p-1557729312269.htm (Year: 2018).*
Walgreens.com—Arm & Hammer Deodorizer Odor Closet Mate. [online] [retr. Aug. 18, 2022] pp. 1-3. htttps://www.walgreens.com/store/c/arm-%26-hammer-deodorizer-odor-closet-mate/ID=300424445-product (Year: 2017).*

* cited by examiner

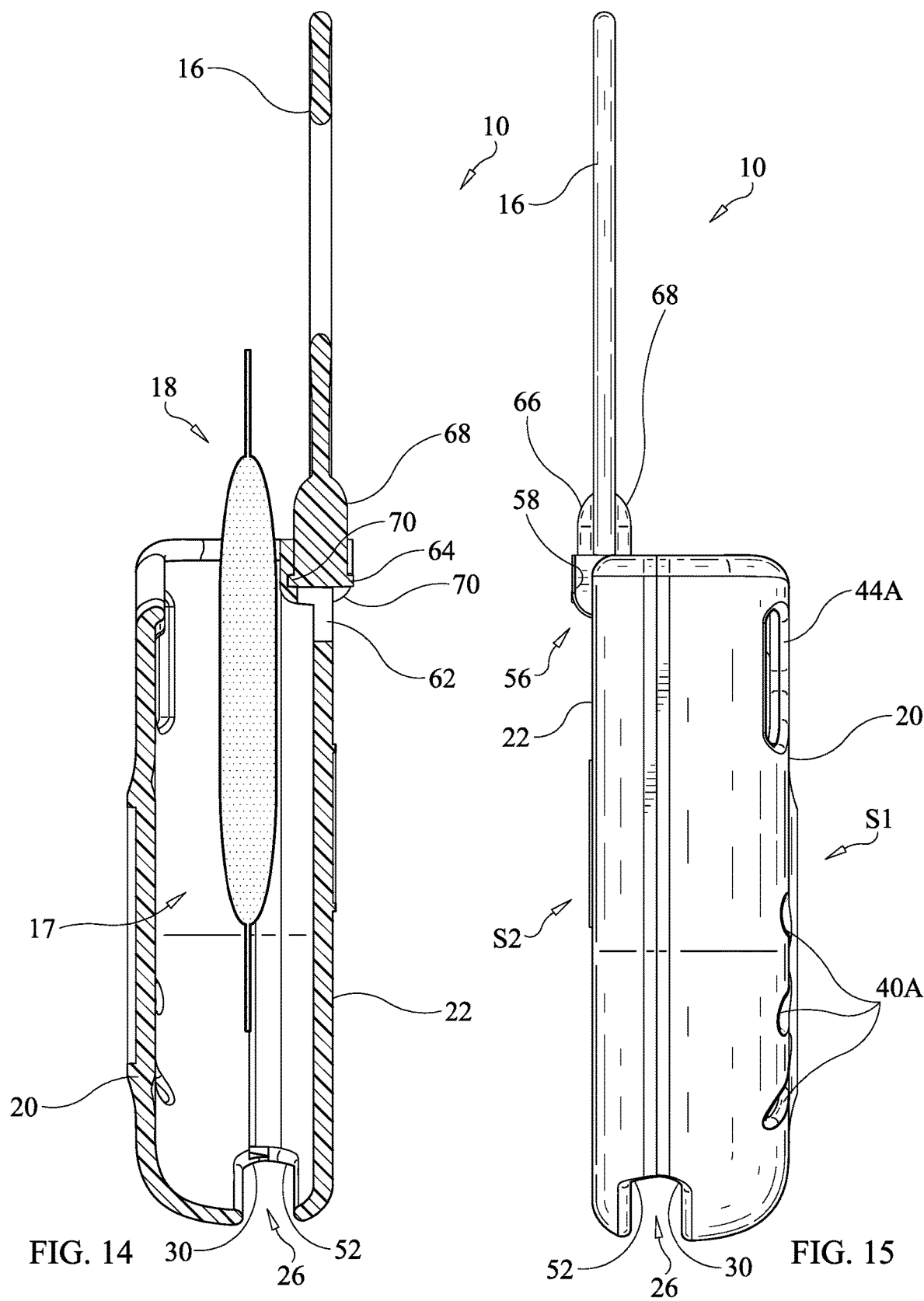

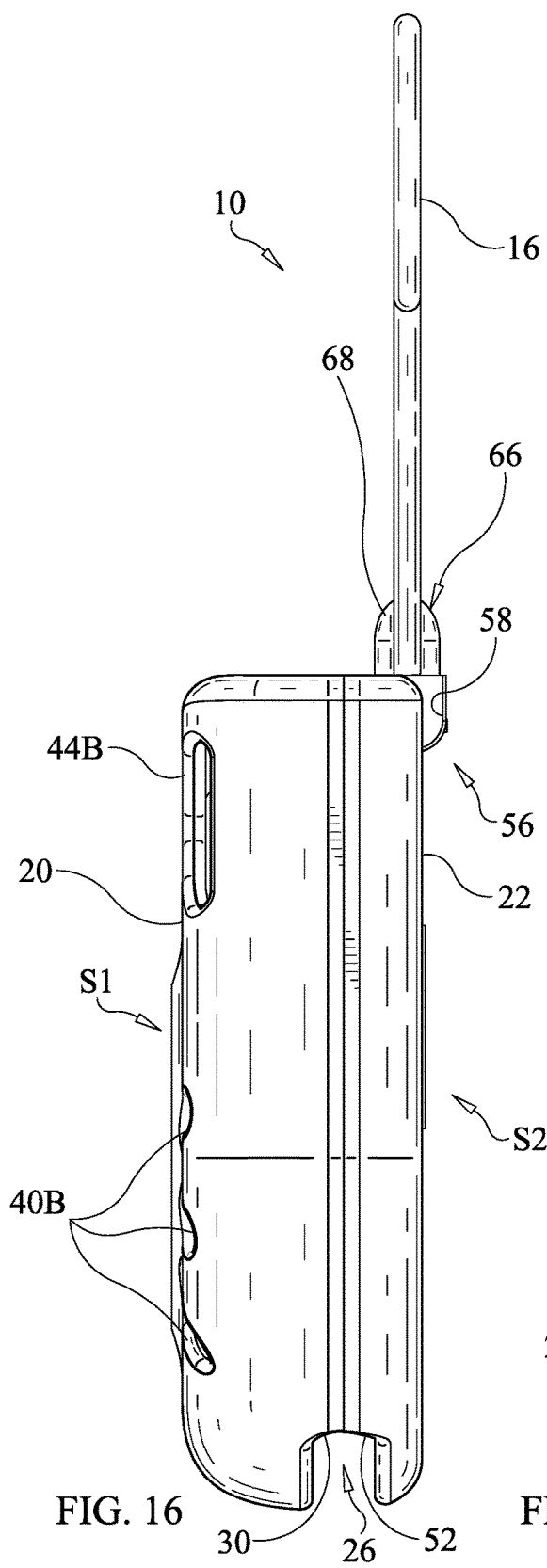
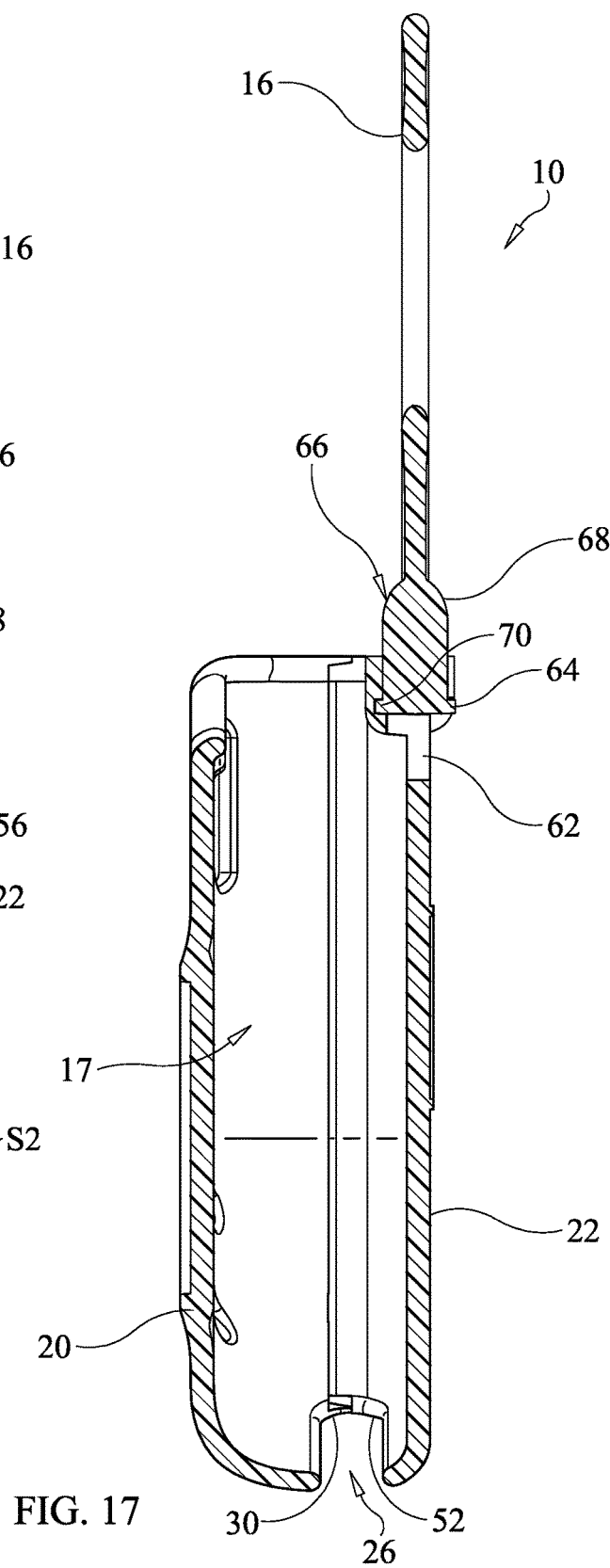
FIG. 16
FIG. 17

ODOR REDUCING DEVICE

CROSS-REFERENCE TO RELATED APPLICATIONS

This application claims priority under 35 U.S.C. § 119 to U.S. Application No. 62/981,174, filed Feb. 25, 2020. The entire disclosure of U.S. Application No. 62/981,174, filed Feb. 25, 2020 is hereby incorporated herein by reference.

BACKGROUND

Field of the Invention

The present invention generally relates to an odor reducing device. More specifically, the present invention relates to an odor reducing device to be provided for a cat litter pan.

Background Information

Conventional cat litter boxes and pans are designed to contain litter and pet waste. Litterboxes can be provided with one or more odor reducing devices to reduce or neutralize odor within the litterbox. For example, odor reducing devices can provide a deodorizing or neutralizing agent for reducing odor within the litterbox.

SUMMARY

In view of the state of the known technology, one aspect of the present disclosure is to provide an odor reducing device for a cat litterbox comprising a housing and a fastener. The housing has a front sidewall and a rear sidewall. The front and rear sidewalls together defines a top opening that opens to an interior of the housing. The fastener is attached to the housing and configured to support the housing on the litterbox.

Also other objects, features, aspects and advantages of the disclosed odor reducing device will become apparent to those skilled in the art from the following detailed description, which, taken in conjunction with the annexed drawings, discloses one embodiment of the odor reducing device.

BRIEF DESCRIPTION OF THE DRAWINGS

Referring now to the attached drawings which form a part of this original disclosure:

FIG. 14 is a cross-sectional view of the odor reducing device having the odor reducing pod;

FIG. 15 is a side view of the odor reducing device similar to FIG. 12 but with the odor reducing pod removed;

FIG. 16 is a side view of the odor reducing device similar to FIG. 13 but with the odor reducing pod removed;

FIG. 17 is a cross-sectional view of the odor reducing device with the odor reducing pod removed;

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

Figure 1:
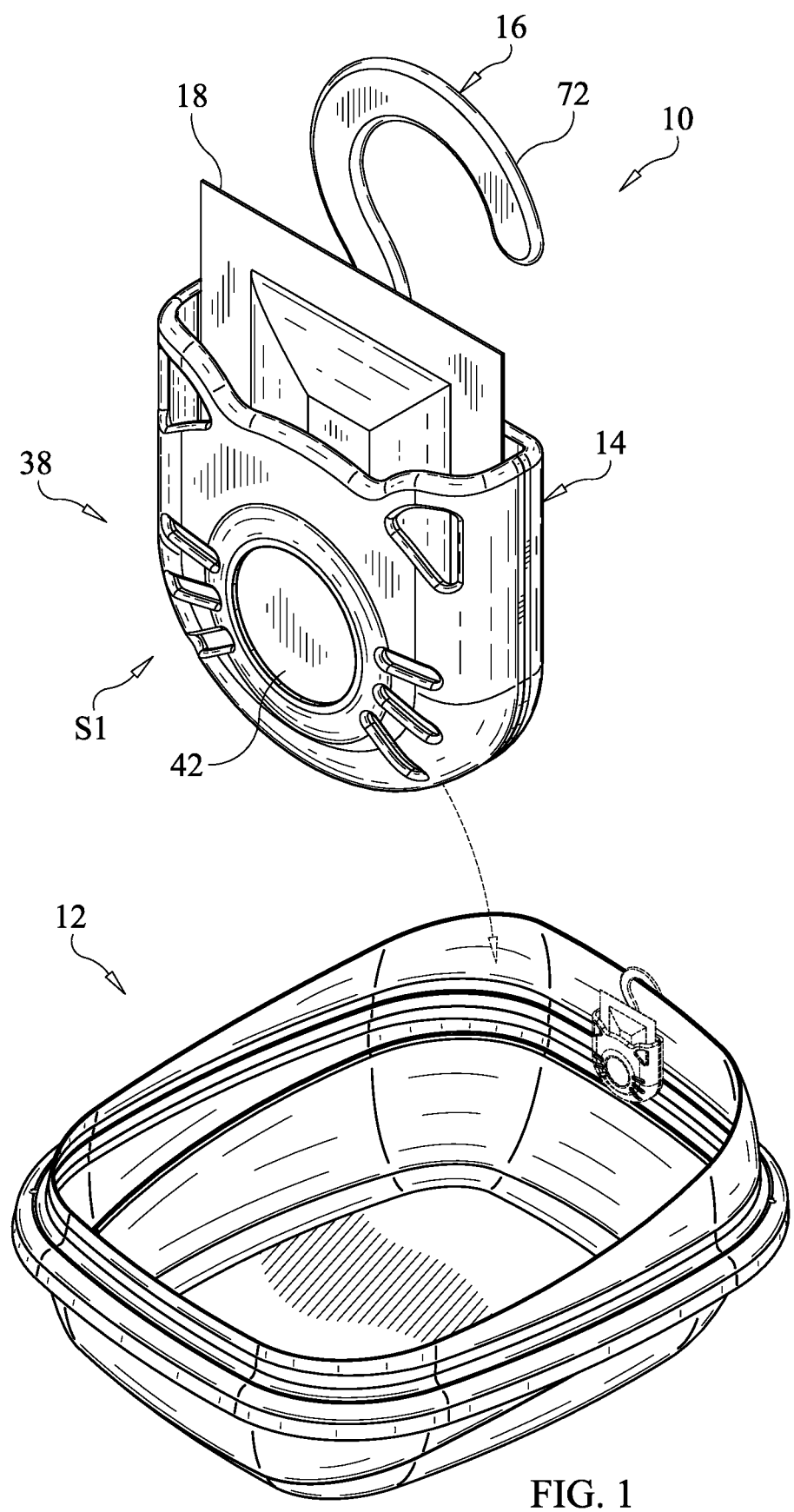
FIG. 1 is a perspective view of a litterbox equipped with an odor reducing device in accordance with an illustrated embodiment.

Referring initially to FIG. 1, an odor reducing device 10 is illustrated in accordance with an illustrated embodiment. The odor reducing device 10 can be used with a cat litterbox 12, as shown. In particular, the odor reducing device 10 is designed to be supported to the litterbox 12, such as to any of the sidewalls of the litterbox 12. In the illustrated embodiment, the odor reducing device 10 comprises a housing 14 and a fastener 16 configured to support the housing 14 on the litterbox 12. As shown, the odor reducing device 10 further comprises an odor reducing pod 18 that is removably disposed in an interior H of the housing 14. The odor reducing pod 18 of the illustrated embodiment serves as a cat deodorizer for the litterbox 12 that neutralizes cat litter odor and to help maintain the litterbox 12 in a fresh and clean condition.

The odor reducing device 10 is designed to house the odor reducing pod 18 and any subsequent refills of the odor reducing pod 18. Therefore, the odor reducing pod 18 is easily removable from the housing 14 for easy replacement of the odor reducing pod 18. The odor reducing pod 18 includes baking soda, and other deodorizing agents and/or odor freshening agents, such as ARM & HAMMER™ baking soda and/or Fresh Scents™ deodorizer. The odor reducing pod 18 of the illustrated embodiment is preferably a rectangular pod having a relatively flat shape. However, it will be apparent to those skilled in the pet products field from this disclosure that the odor reducing pod 18 can have different shapes and sizes to be disposed in the housing 14 as needed and/or desired.

Figure 3:
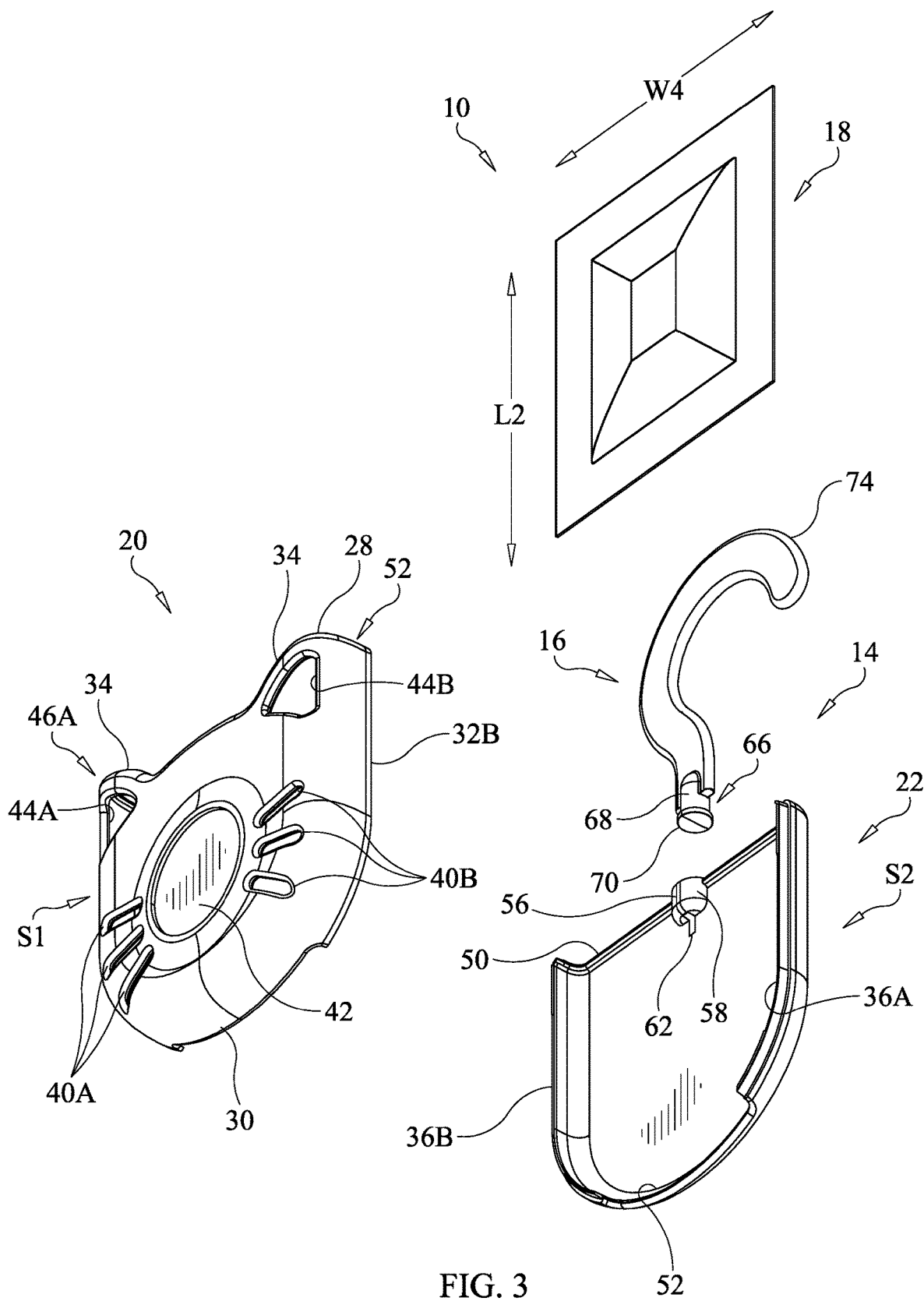
FIG. 3 is an exploded view of the odor reducing device.
Figure 4:
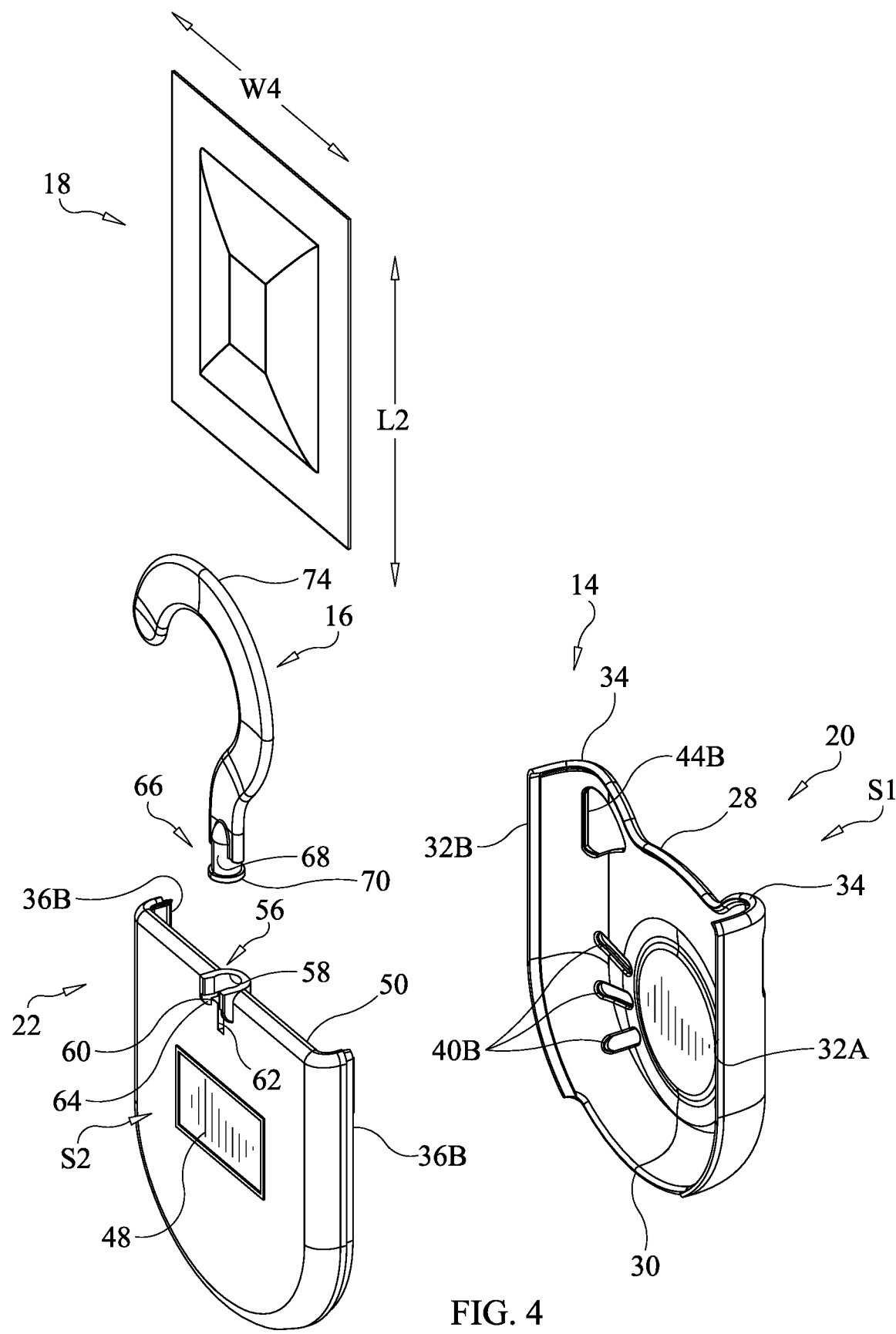
FIG. 4 is another exploded view of the odor reducing device.

Referring to FIGS. 3 and 4, the housing 14 has a front sidewall 20 and a rear sidewall 22. The front sidewall 20 defines a front face S1 (as shown in FIG. 3) of the housing 14. The front face S1 is a front surface that preferably faces toward the interior of litterbox 12 when the odor reducing pod 18 is installed to the litterbox 12. The rear sidewall 22 defines a rear face S2 of the housing 14 (as shown in FIG.

4). The rear face S2 is a rear surface that preferably faces away from the interior of the litterbox 12 when the odor reducing pod 18 is installed to the litterbox 12. Therefore, the front and rear face S2s of the housing 14 are oppositely facing surfaces of the housing 14. Together, the front sidewall 20 and the rear sidewall 22 are mating housing components that couple together to define the interior H of the housing 14.

Figure 2:
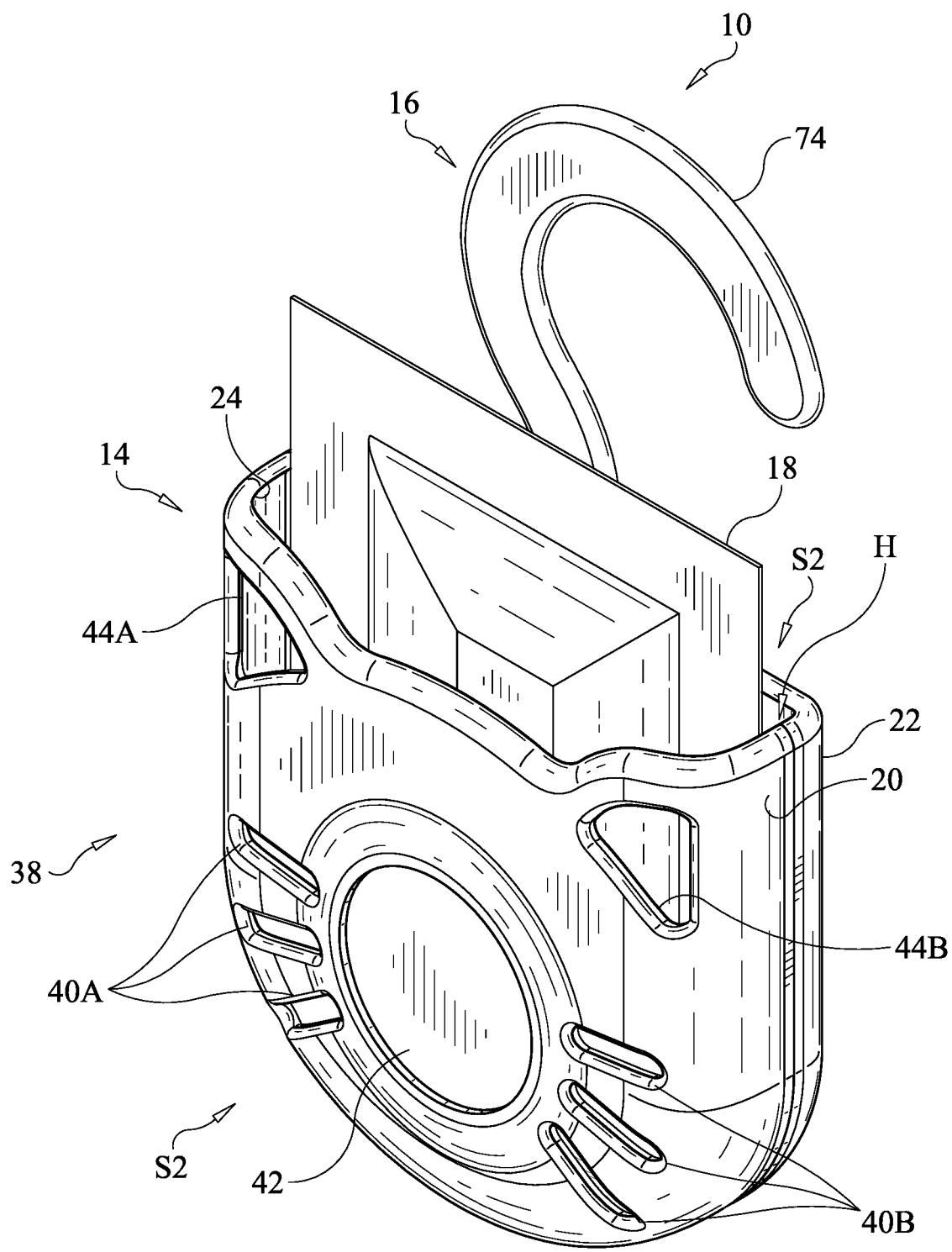
FIG. 2 is a perspective view of the odor reducing device of FIG. 1.
Figure 6:
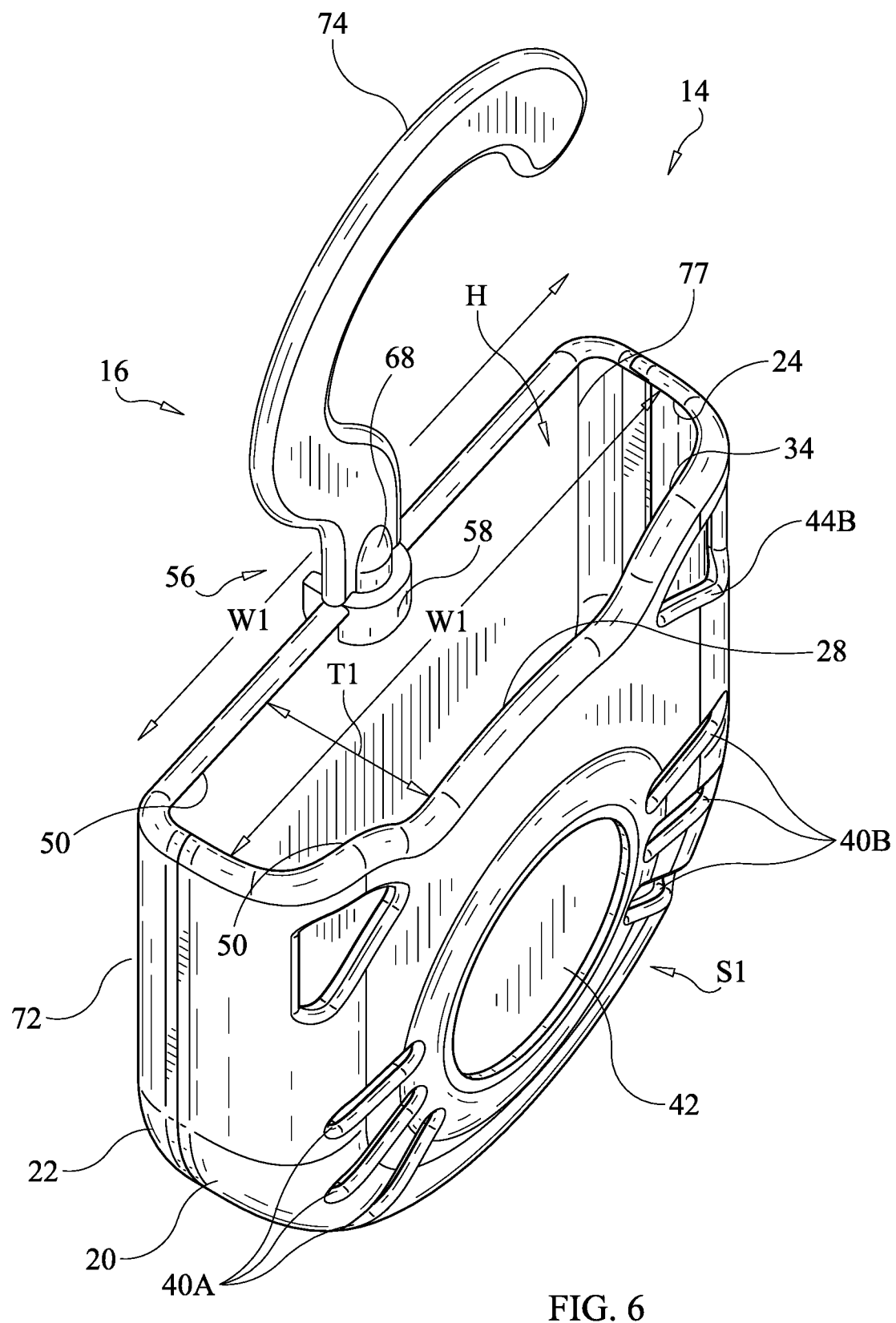
FIG. 6 is a top perspective view of the odor reducing device with an odor reducing pod removed.

The front and rear sidewalls 20 and 22 are detachably attached to each other. In particular, the front and rear sidewalls 20 and 22 can be coupled to each other by snap-fit or by clips, such as shown in FIGS. 14 and 17. When the front and rear sidewalls 20 and 22 are coupled together, the front and rear sidewalls 20 and 22 form a hollow housing 14 body with a top opening that is a top slot 24, and a bottom opening that is a bottom slot 26. Therefore, as best seen in FIGS. 2 and 6, the front and rear sidewalls 20 and 22 together define the top slot 24 that receives the odor reducing pod 18 and opens to the interior H of the housing 14. Therefore, the odor reducing pod 18 is removably disposed in the interior H of the housing 14 through the top slot 24.

The top slot 24 is sized and dimensioned to enable the odor reducing pod 18 to pass therethrough and into the interior H of the housing 14. Preferably, as best seen in FIG. 6, the top slot 24 forms substantially an upper portion of the housing 14. That is, the top slot 24 has a maximum width W1 that is substantially equal to a maximum width W2 of the housing 14 but slightly less due to the thickness of the front and rear sidewalls 20 and 22. The top slot 24 has a maximum thickness T1 that is a substantially equal to a maximum thickness T2 of the housing 14 but slightly less due to the thickness of the front and rear sidewalls 20 and 22.

As shown in FIGS. 1 to 5, the odor reducing pod 18 is preferably sized and dimensioned to enter through the top slot 24 to sit within the interior H of the housing 14. Preferably, a portion of the odor reducing pod 18 can extend upwards out of the top slot 24 to enable easy removal and replacement of the odor reducing pod 18 from the housing 14. Therefore, the housing 14 preferably has a maximum length L1 that is less than a maximum length L2 of the odor reducing pod 18.

As seen in FIGS. 9 and 11 to 17, the front and rear sidewalls 20 and 22 together define the bottom slot 26. The bottom slot 26 preferably forms a flat lip of the bottom of the housing 14, as best seen in FIGS. 12-17. The bottom slot 26 has a maximum width W3 that is less than a maximum width W4 of the odor reducing pod 18. Therefore, the maximum width W3 of the bottom slot 26 is smaller than the maximum width W1 of the top slot 24 in the illustrated embodiment. In this way, the bottom slot 26 enables the odor reducing device 10 to stand in the interior H of the housing 14. However, the bottom slot 26 is sized and dimensioned to enable debris such as cat litter to pass therethrough. The front and rear sidewalls 20 and 22 together form the bottom slot 26 once coupled together.

As shown in FIG. 1, the fastener 16 is attached to the housing 14 so that the front surface S1 faces towards the litterbox's 12 interior and the rear surface S2 faces towards the litterbox's 12 exterior when the odor reducing device 10 is supported to the litterbox 12. In particular, the fastener 16 is attached to the rear sidewall 22 to support the housing 14 to the litterbox 12, as will be further discussed below.

Figure 5:
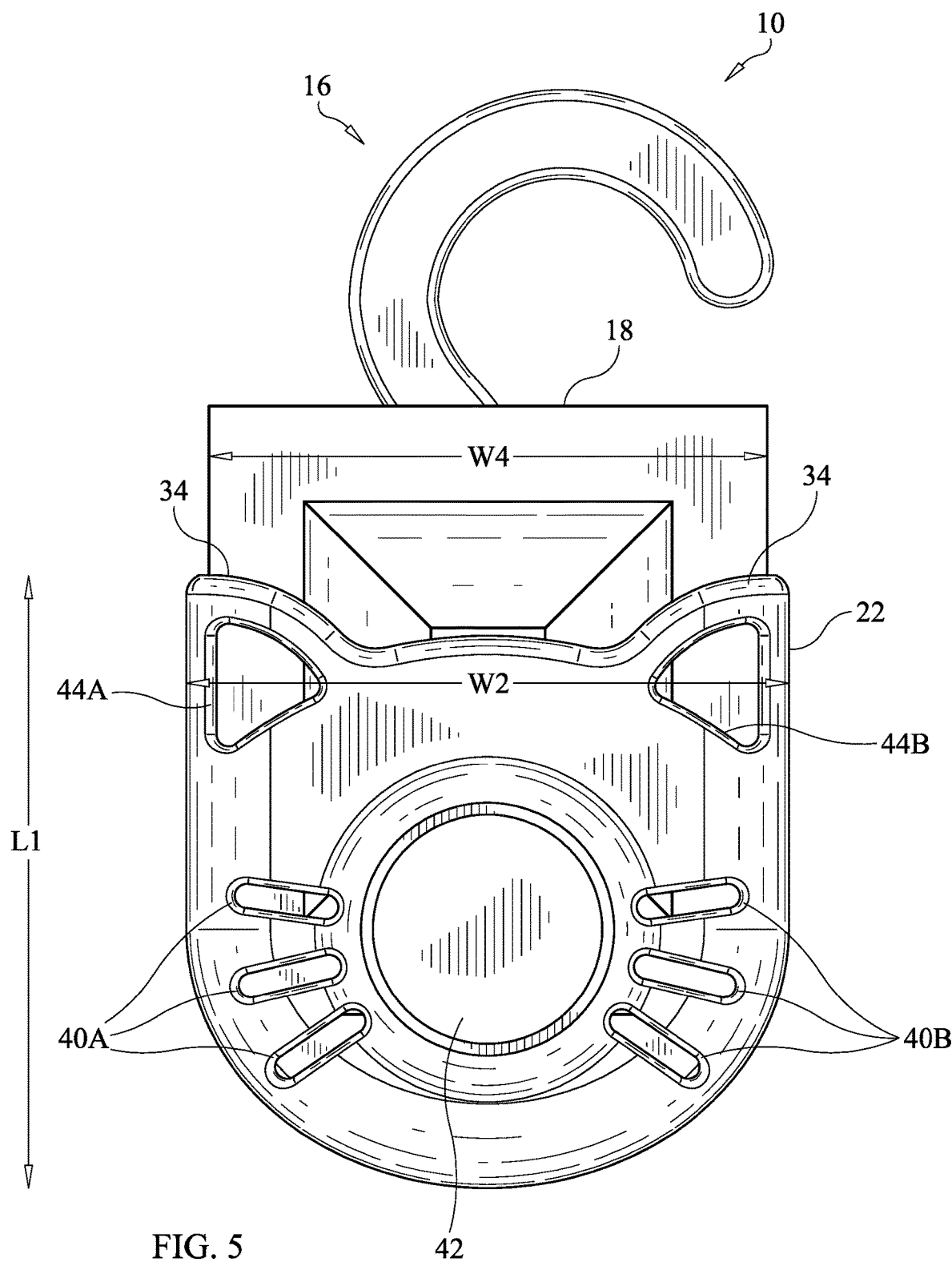
FIG. 5 is a plan view of a frontside of the odor reducing device.
Figure 7:
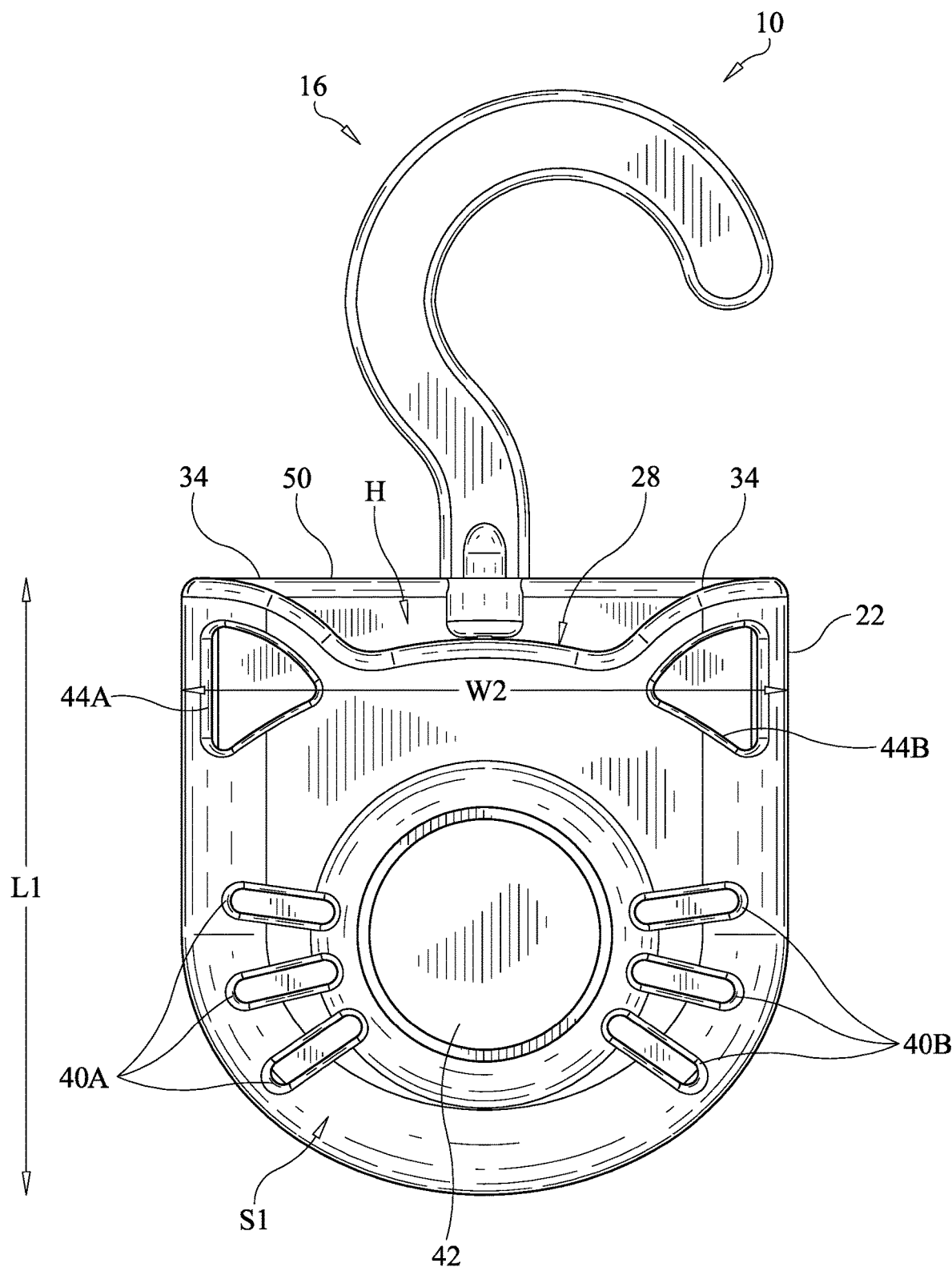
FIG. 7 is a plan view of the frontside of the odor reducing device of FIG. 6.
Figure 8:
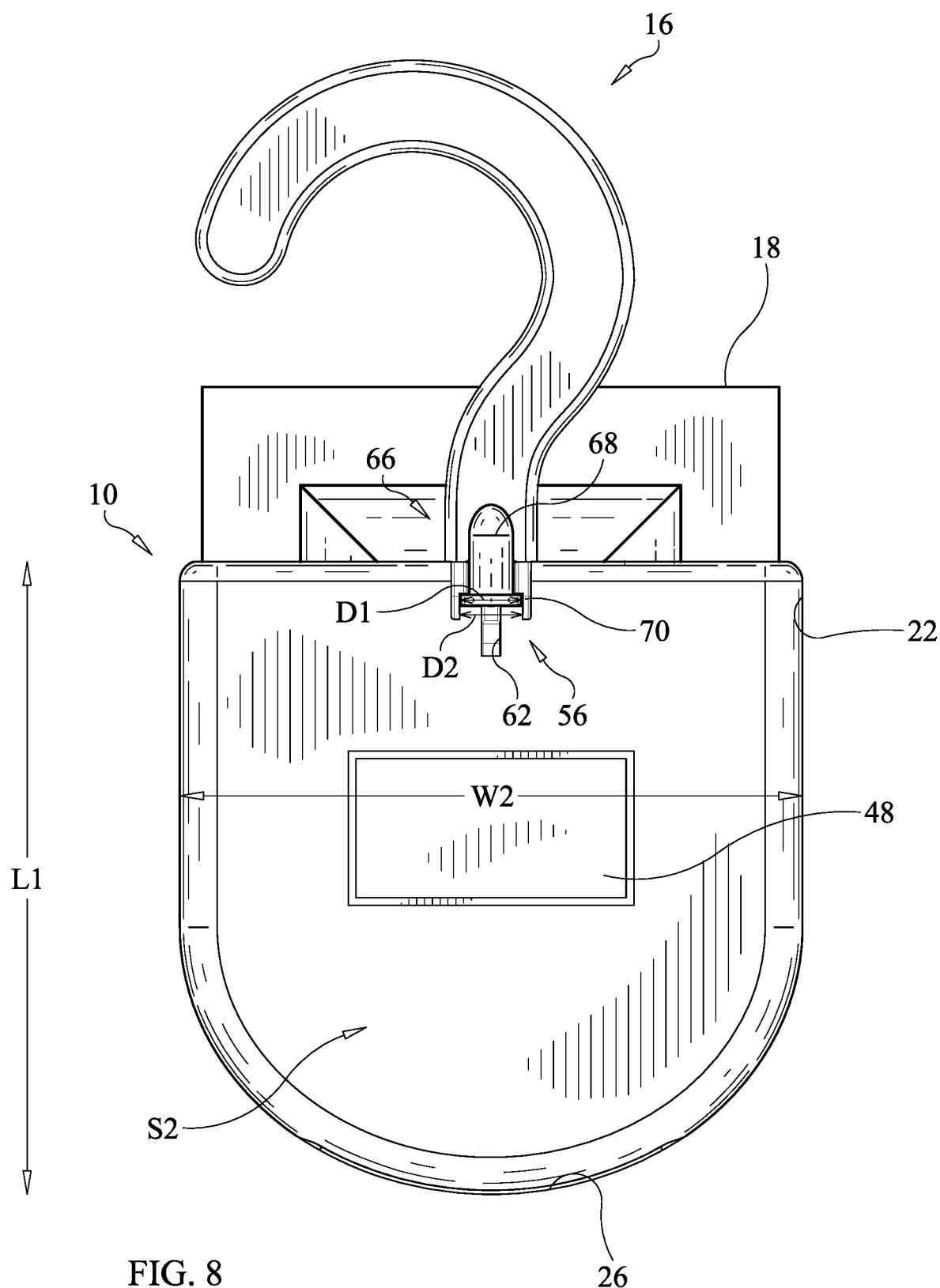
FIG. 8 is a plan view of the backside of the odor reducing device having the odor reducing pod.

As best seen in FIG. 4, the front face S1 is an outer (exterior) face of the housing 14. The front sidewall 20 has a top edge 28, a bottom edge 30 and a pair of first side edges 32A and 32B. The top and bottom edges 28 and 30 are connected by the first side edges 32A and 32B in a lengthwise direction of the housing 14. The top edge 28 curves away from the side edges 32A and 32B towards the front face S1 of the front sidewall 20. The top edge 28 forms the top slot 24 with the rear sidewall 22. As best seen in FIGS. 4, 5 and 7, the top edge 28 can include a pair of upwardly curving portions 34. In the illustrated embodiment, the upwardly curving portions 34 are designed to look like cat ears.

Figure 9:
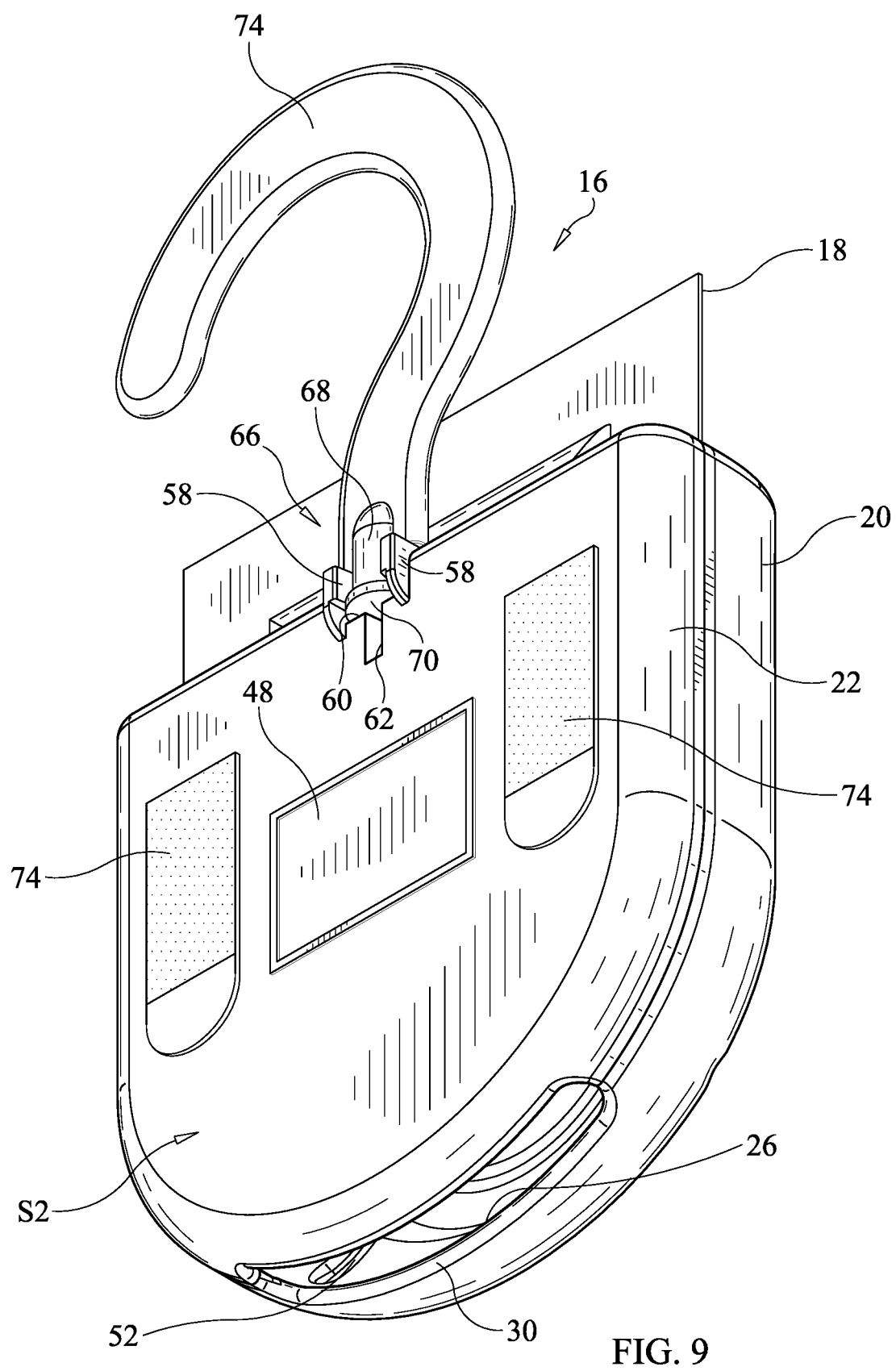
FIG. 9 is a bottom perspective view of the odor reducing device of FIG. 8.
Figure 10:
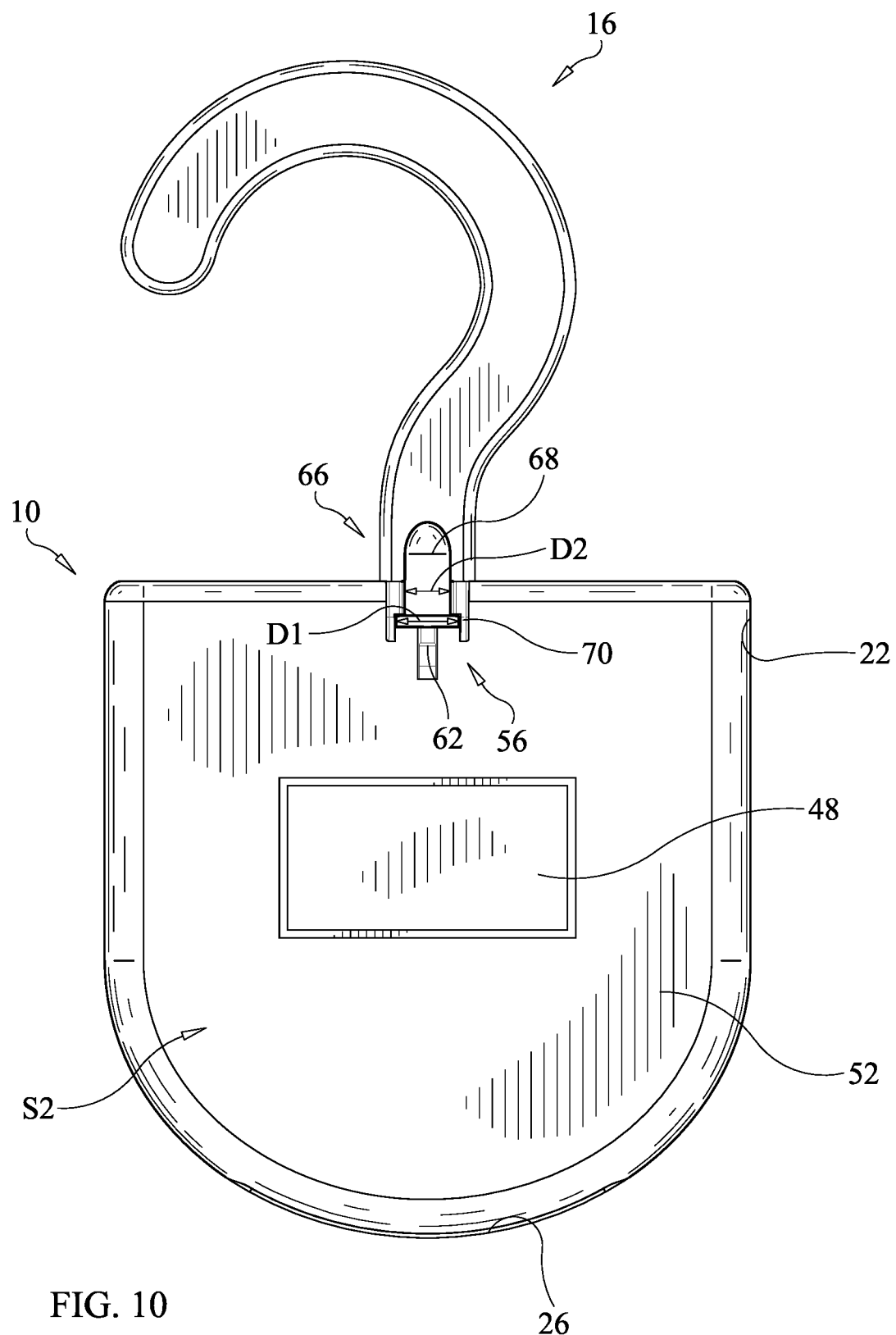
FIG. 10 is a plan view of the backside of the odor reducing device with the odor reducing pod removed.
Figure 11:
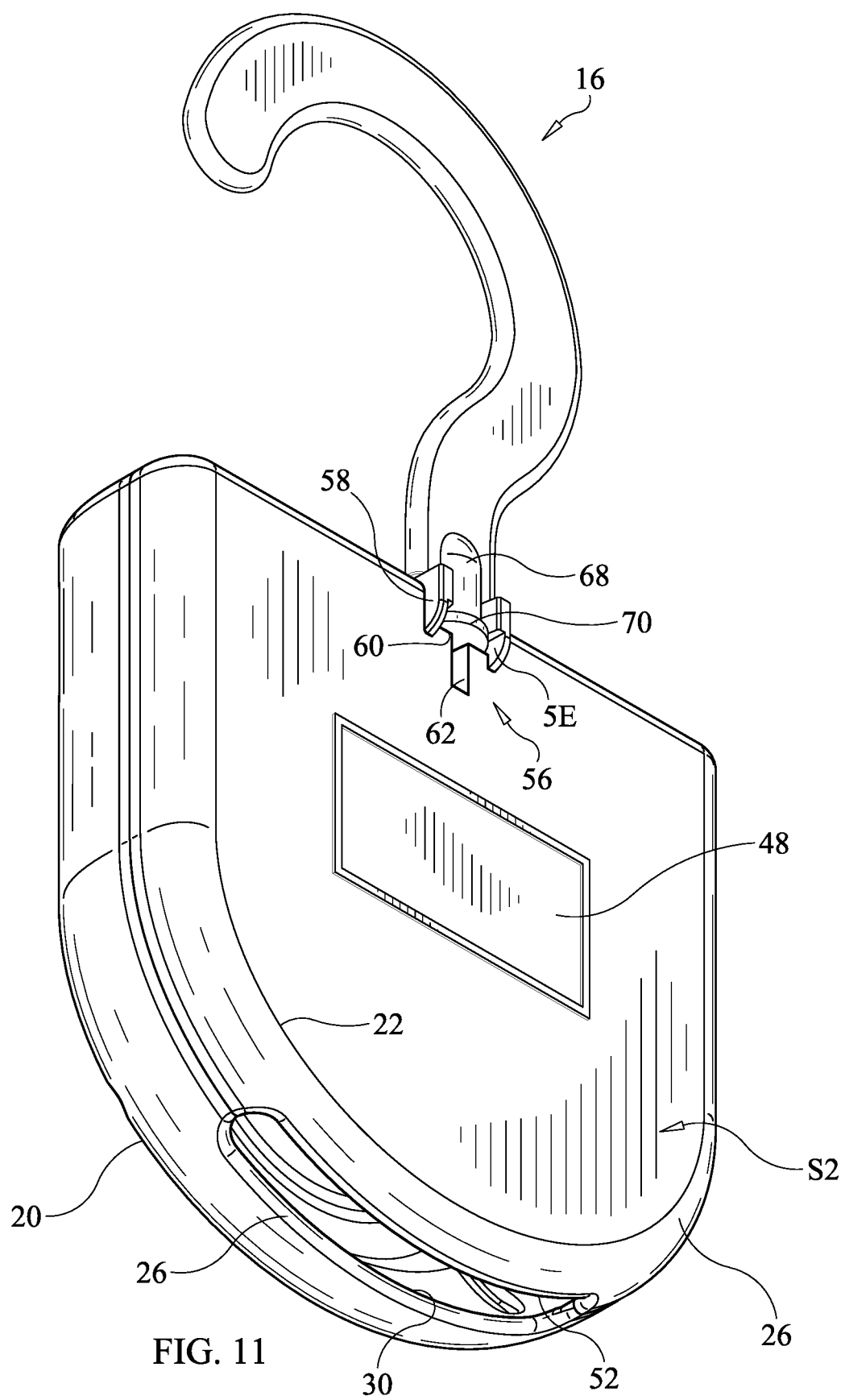
FIG. 11 is a bottom perspective view of the odor reducing device of FIG. 10.
Figure 12:
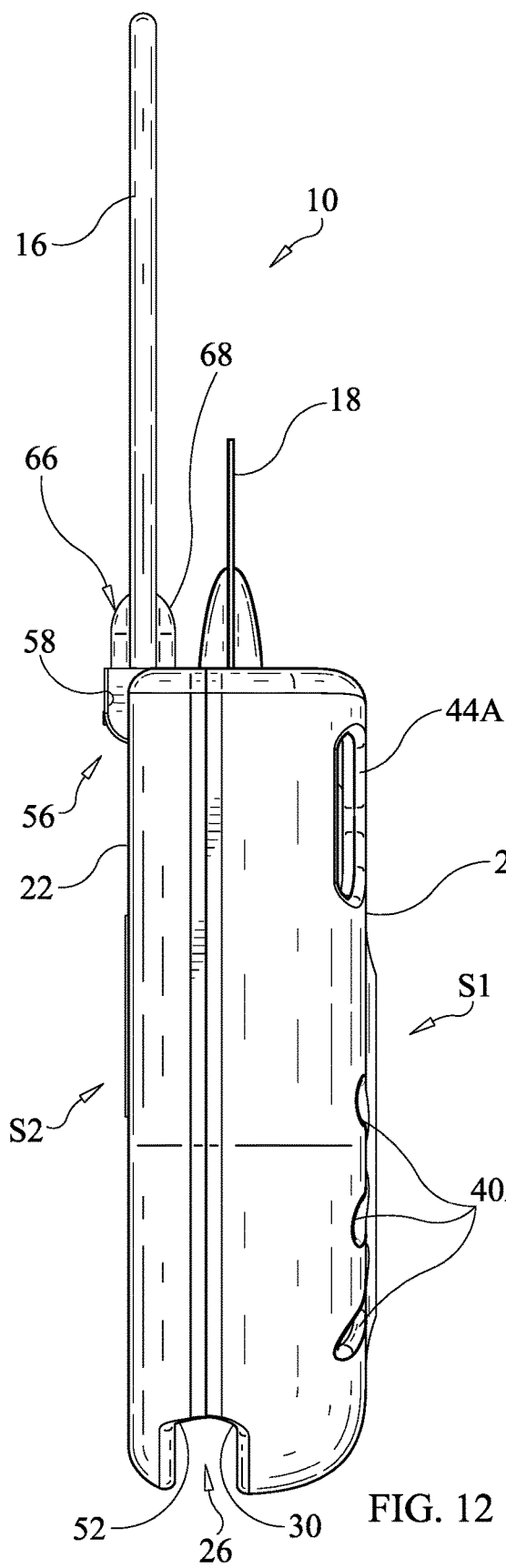
FIG. 12 is a side view of the odor reducing device having the odor reducing pod.
Figure 13:
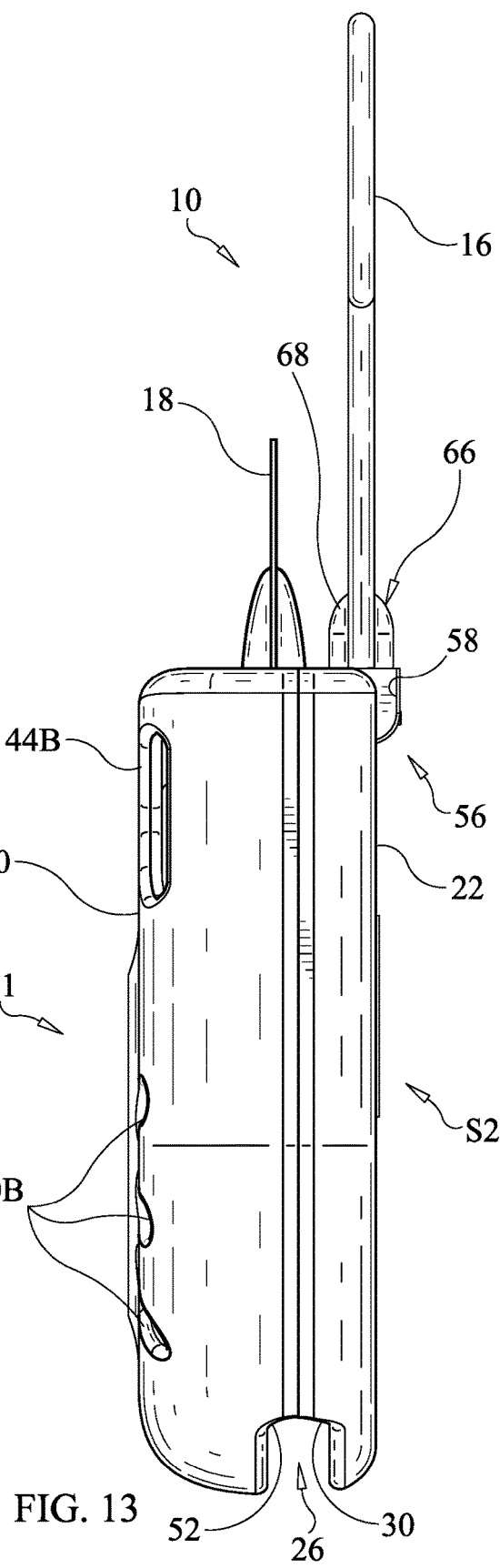
FIG. 13 is another side view of the odor reducing device having the odor reducing pod.
Figure 18:
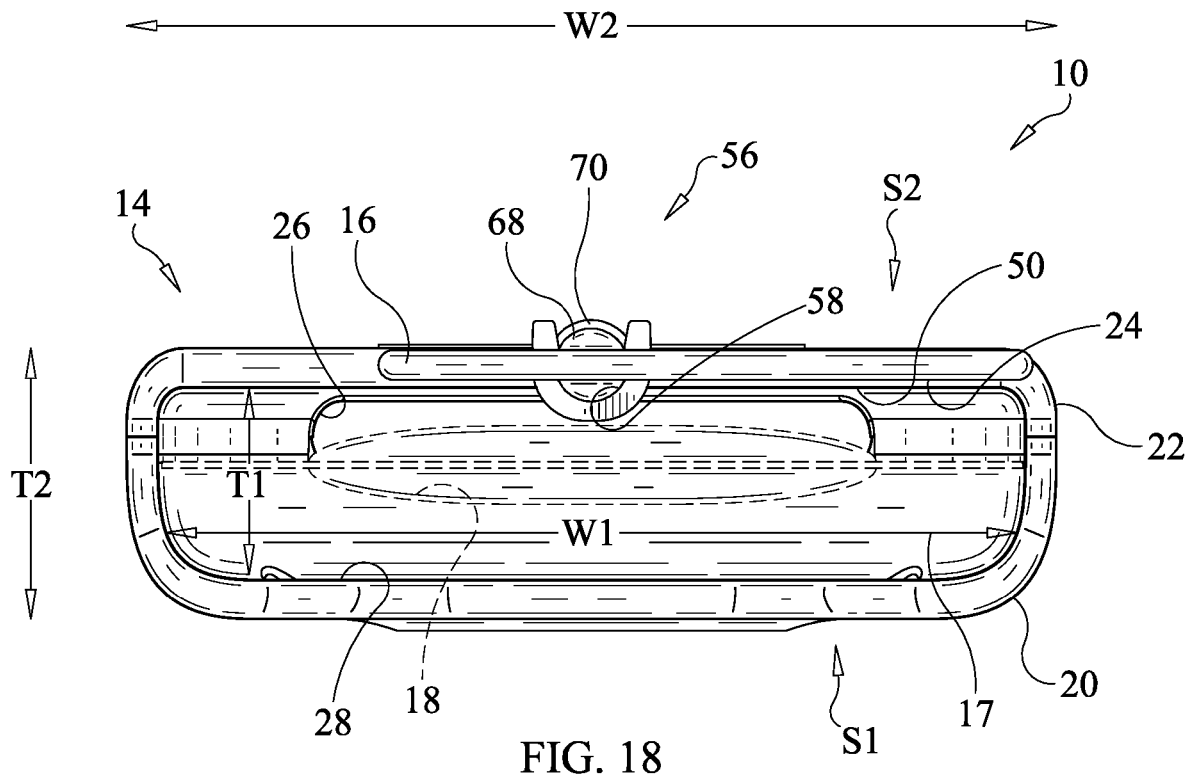
FIG. 18 is a plan view of a top of the odor reducing device having the odor reducing pod.
Figure 19:
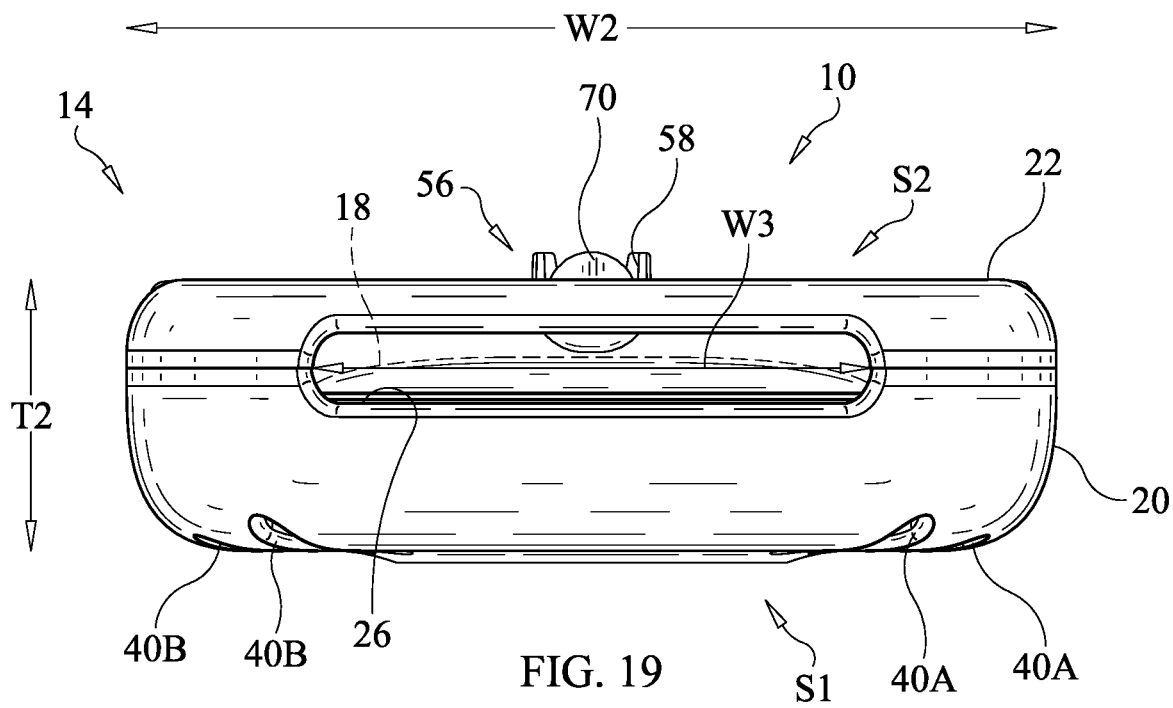
FIG. 19 is a plan view of a bottom of the odor reducing device having the odor reducing pod.
Figure 20:
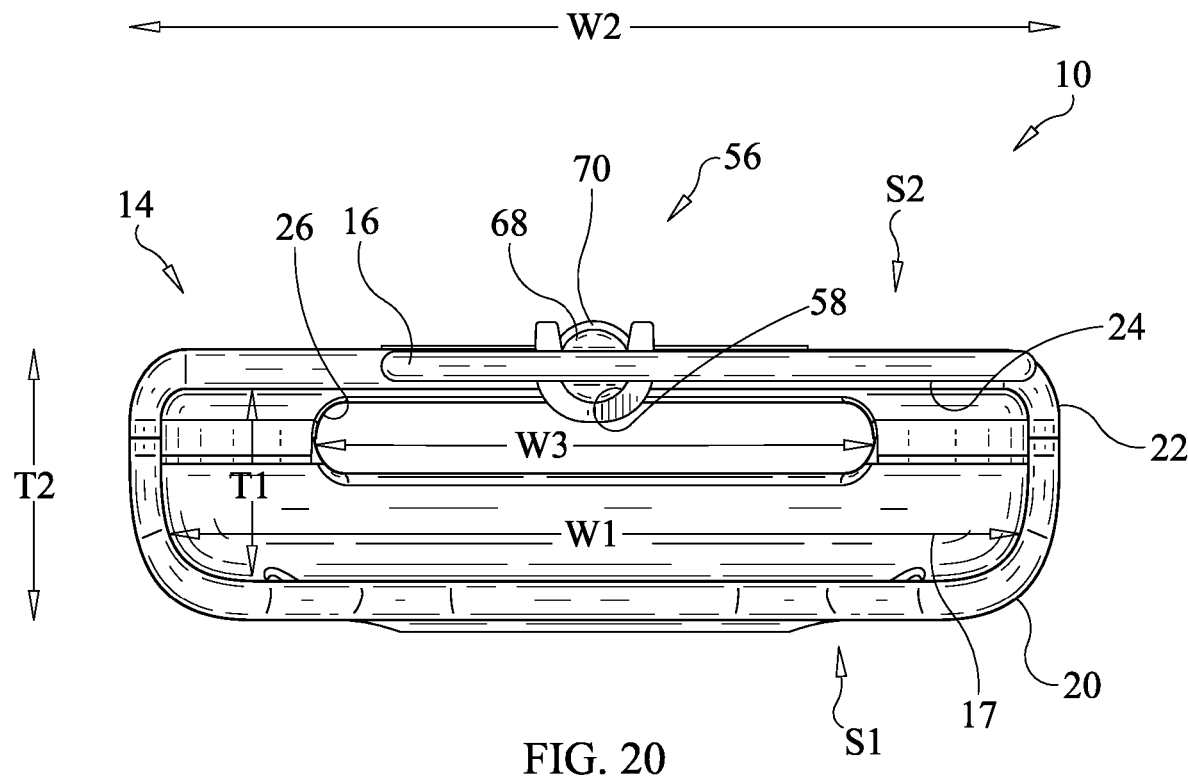
FIG. 20 is a plan view of a top of the odor reducing device with the odor reducing pod removed.
Figure 21:
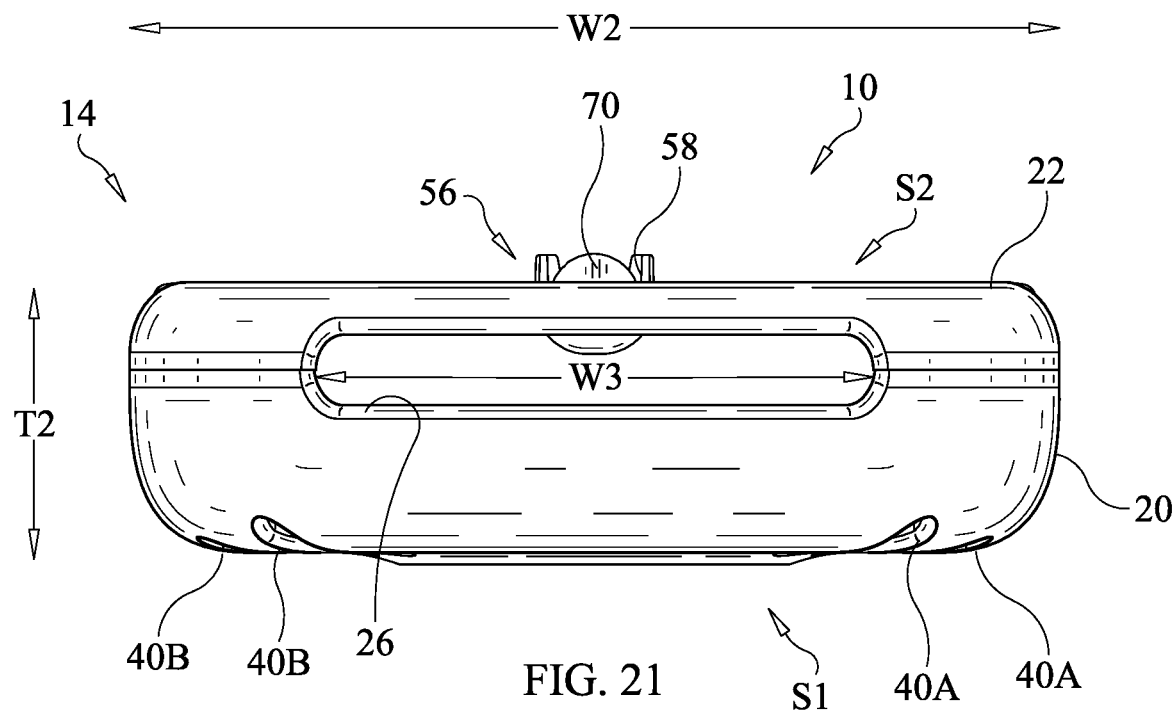
FIG. 21 is a plan view of a bottom of the odor reducing device with the odor reducing pod removed.

As best seen in FIGS. 4, 9 and 11, the bottom edge 30 is recessed away from the first side edges 32A and 32B in a direction towards the front face S1 to help form the bottom slot 26 with the rear sidewall 22. The bottom edge 30 is curved downwardly with respect to the first side edges 32A and 32B. The first side edges 32A and 32B of the front sidewall 20 are configured to detachably connect to a pair of corresponding second side edges 36A and 36B of the rear sidewall 22. Therefore, the front sidewall 20 includes the first side edges 32A and 32B. The rear sidewall 22 includes the second side edges 36A and 36B that correspond to the first side edges 32A and 32B to detachably connect to the front sidewall 20 along the first and second side edges 32A, 32B, 36A and 36B. As seen in one embodiment illustrated in FIGS. 14 and 17, the first and second side edges 32A, 32B, 36A and 36B have mating surfaces that clips or fastens to each other in a conventional manner, such as by snap-fit.

As best seen in FIGS. 2 and 5 to 7, the front sidewall 20 includes a plurality of vents 38 that open to the interior H of the housing 14. The vents 38 can be openings in the front face S1 of the front sidewall 20 to connect the interior H of the housing 14 with the exterior. The vents 38 are air flow vents that enable the odor reducing pod 18 to transmit air flow from the interior H of the housing 14 into the litterbox 12. In the illustrated embodiment, the plurality of vents 38 includes at least one elongated opening 40A and 40B. In particular, the plurality of vents 38 includes two sets of elongated opening 40A and 40B, each set comprising three elongated openings in the illustrated embodiment. It will be apparent to those skilled in the pet products field from this disclosure that the vents 38 can include other types of openings of different shapes, sizes, numbers and arrangements.

As best seen in FIGS. 2 and 3, the front sidewall 20 includes a circular recess 42 on the front face S1 of the front sidewall 20. The circular recess 42 can be used for fixing or adhering indicia (such as logos, instructions, decorations, etc.) thereon. In the illustrated embodiment, the elongated openings 40A and 40B are arranged adjacent to the circular recess 42 and extend radially away from the circular recess 42. The arrangement of the elongated openings 40A and 40B and the circular recess 42 create the appearance of cat whiskers on the front face S1 of the housing 14.

As shown, the plurality of vents 38 includes a first set of elongated opening 40A disposed adjacent to a first lateral side of the circular recess 42. The first set of elongated openings 40A extend radially away from the circular recess 42 towards the side edge 32A. The plurality of vents 38 includes a second set of elongated openings 40B disposed adjacent to a second lateral side of the circular recess 42. The first and second lateral sides are opposite of each other. The second elongated openings 40B extend radially away from the circular recess 42 towards the side edges 32B. In the illustrated embodiment, the each set of the elongated openings 40A and 40B include three elongated openings. However, it will be apparent to those skilled in the pet products field from this disclosure that the housing 14 can include different numbers of elongated openings of different sizes and arrangements as needed and/or desired.

As best seen in FIGS. 5 to 7, the plurality of vents 38 preferably further include a pair of triangular openings 44A and 44B. The front sidewall 20 includes a first triangular opening 44A that is disposed on a first top side of the front sidewall 20 by one of the curving portions 34. The front sidewall 20 further includes a second triangular opening 44B that is disposed on a second top side of the front sidewall 20 by the other one of the curving portions 34. The first and second top sides are opposite with respect to another along the front sidewall 20. The arrangement of the triangular openings 44A and 44B create a general appearance of animal ears (e.g., cat ears) on the housing 14. Thus, the overall shape of the housing 14 having the vents 38 at the front face S1 give the housing 14 a general cat-like appearance.

As seen in FIGS. 3, 4 and 8 to 11, the rear sidewall 22 is preferably devoid of vents. However, it will be apparent to those skilled in the pet products field from this disclosure that, if desired, the rear sidewall 22 can include a vent or a plurality of vents. The rear face S2 of the rear sidewall 22 can include a depression 48 or recess for placing indicia, or an adhesion device (e.g., double sided tape), as needed and/or desired. As best seen in FIGS. 3 and 4, the rear sidewall 22 has a top edge 50, a bottom edge 52 and the second side edges 36A and 36B. The top and bottom edges 50 and 52 are connected by the second side edges 36A and 36B in the length-wise direction of the housing 14. The second side edges 36A and 36B mate with the first side edges 32A and 32B to form the housing 14. The top edge 50 curves away from the second side edges 36A and 36B towards the rear face S2 of the rear sidewall 22. The top edge 50 forms the top slot 24 with the front sidewall 20.

As best seen in FIGS. 3, 9, 11 to 17, 19 and 21, the bottom edge 52 of the rear sidewall 22 the bottom edge 52 is recessed away from the second side edges 36A and 36B towards the rear face S2 to help form the bottom slot 26 with the front sidewall 20. The bottom edges 52 of the front and rear sidewalls 20 and 22 together form the bottom slot 26. The bottom edge 52 of the rear sidewall 22 is curved downwardly with respect to the second side edges 36A and 36B. As stated, the first side edges 32A and 32B of the front sidewall 20 are configured to mate with the second side edges 36A and 36B of the rear sidewall 22.

As shown, the fastener 16 is attached to the rear sidewall 22. As best seen in FIGS. 3 and 4, the rear sidewall 22 includes a fastener attachment part 56 that receives the fastener 16 therethrough. As best seen in FIGS. 14 and 17, the fastener attachment part 56 preferably leads to a hollow area having a cylindrical backwall 58 that protrudes from the rear sidewall 22 at the top edge towards the housing 14 interior. As best seen in FIGS. 3, 4 and 9 to 11, the fastener attachment part 56 has a bottom surface 60 with a slotted opening 62. The fastener attachment part 56 includes a channel 64 along the cylindrical backwall 58 along the bottom surface 60 that forms a space between the cylindrical backwall 58 and the bottom surface 60.

As seen in FIG. 4, the fastener attachment part 56 opens at the top edge 50 and on the rear face S2 to receive the fastener 16. It will be apparent to those skilled in the pet products field from this disclosure that the cylindrical backwall 58 can alternatively protrude towards the housing's 14 exterior so that the fastener attachment part 56 can open at the interior facing side to receive the fastener 16. Additionally, it will be further apparent to those skilled in the pet products field from this disclosure that the fastener attachment part 56 can be disposed on other parts of the housing 14, such as to the front sidewall 20 or on the rear face S2 of the housing 14 as needed and/or desired.

The fastener 16 is attached to the housing 14 at the fastener attachment part 56. As best seen in FIGS. 9, 11, 14 and 17, the fastener 16 has a base 66 that is fixed to the fastener attachment part 56. The base 66 has a cylindrical body 68 with a circular bottom 70. The circular bottom 70 has a maximum diameter D1 that is larger than a maximum diameter D2 of the cylindrical body 68. The cylindrical body 68 is fitted to the fastener attachment part 56 such that the circular bottom 70 is received within the channel 64 of the fastener attachment part 56. The circular bottom 70 is preferably fitted into the channel 64 by interference fit to allow some degree of rotational movement of the fastener 16 once attached within the fastener attachment part 56. Therefore, the fastener 16 and the housing 14 are rotatable with respect to each other about the base 66 of the fastener 16. Therefore, the fastener 16 is rotatably attached to the rear sidewall 22.

In the illustrated embodiment, the fastener 16 includes a hook 72 that is an attaching member that attaches the odor reducing device 10 to the litterbox 12. In the illustrated embodiment, the attaching member is preferably a plastic hook 72 that is removably coupled or attached to the housing 14. However, it will be apparent to those skilled in the pet products field from this disclosure that the fastener 16 can alternatively have a clip (not shown) that can be clipped to the litterbox 12 to couple the housing 14 to the litterbox 12. For example, the hook 72 can be replaced with a spring-loaded clip such as a carabiner that clips over a lip of the litterbox 12 or an opening in in the sidewall of the litterbox 12.

Alternatively, odor reducing device 10 can be provided with an adhesive 74 for attaching the housing 14 to the litterbox 12. It will be apparent to those skilled in the pet products field from this disclosure that the fastener 16 can be replaced with an adhesive 74 applied to the rear face S2 of the housing 14. For example, the adhesive 74 can be double-sided tape or the like to attach the housing 14 to the litterbox 12. The adhesive 74 can be applied to the rear face S2 of the housing 14 to attach the housing 14 to the litterbox 12.

General Interpretation of Terms

In understanding the scope of the present invention, the term "comprising" and its derivatives, as used herein, are intended to be open ended terms that specify the presence of the stated features, elements, components and/or groups, but do not exclude the presence of other unstated features, elements, components and/or groups. The foregoing also applies to words having similar meanings such as the terms, "including", "having" and their derivatives. Also, the terms "part," "section," "portion," "member" or "element" when used in the singular can have the dual meaning of a single part or a plurality of parts. Also as used herein to describe the above embodiment(s), the following directional terms "forward", "rearward", "above", "downward", "vertical", "horizontal", "below" and "transverse" as well as any other similar directional terms refer to those directions of the odor reducing device. Accordingly, these terms, as utilized to describe the present invention should be interpreted relative to the odor reducing device.

The term "configured" as used herein to describe a component, section or part of a device that is constructed to carry out the desired function.

The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

What is claimed is:

1. An odor reducing device for a cat litterbox, comprising:
    a housing having a front sidewall facing away from a wall of the litterbox when installed onto the litterbox and a rear sidewall facing towards the wall of the litterbox when installed onto the litterbox, the front and rear sidewalls together defining a pair of lateral sides of the housing, a top opening that is a continuous slot extending longitudinally between the lateral sides of the housing, the continuous slot opens to an interior of the housing, the top opening receiving an odor reducing pod into the interior, the front and rear sidewalls together further defining a bottom opening that is smaller than the top opening, the top and bottom openings facing in opposite directions with respect to each other, the top opening being a singular opening defining substantially an entirety of a top of the housing so that the odor pod can be disposed within the interior of the housing and protruding through the top opening, the front sidewall having a plurality of airflow vents that enable the odor reducing pod to transmit air flow from the interior of the housing into the litterbox, the rear sidewall being devoid of an air flow vent; and
    a hook detachably attached to the housing and configured to support the housing on the litterbox, the hook being rotatable with respect to the housing.
2. The odor reducing device according to claim 1, further comprising
    the odor reducing pod removably disposed in the interior of the housing through the top opening.
3. The odor reducing device according to claim 2, wherein the bottom opening has a maximum width that is less than a maximum width of the odor reducing pod.
4. The odor reducing device according to claim 1, wherein the hook is attached to the rear sidewall so that the front sidewall faces towards a litterbox interior and the rear sidewall faces a litterbox exterior when the odor reducing device is supported to the litterbox.
5. The odor reducing device according to claim 4, wherein the hook is rotatably attached to the rear sidewall.
6. The odor reducing device according to claim 1, wherein the front sidewall has a pair of first side edges, the rear sidewall has a pair of second side edges that correspond to the pair of first side edges to connect to the front sidewall along the pair of first and second side edges.
7. The odor reducing device according to claim 1, wherein the plurality of airflow vents includes at least one elongated opening.
8. The odor reducing device according to claim 7, wherein the front sidewall includes a circular recess on a front surface of the front sidewall.
9. The odor reducing device according to claim 8, wherein the plurality of airflow vents includes a plurality of first elongated openings disposed adjacent to a first lateral side of the circular recess, and a plurality of second elongated openings disposed adjacent to a second lateral side of the circular recess, the first and second lateral sides being opposite of each other.
10. The odor reducing device according to claim 9, wherein the plurality of airflow vents further include a pair of triangular openings.
11. The odor reducing device according to claim 10, wherein
    a first triangular opening of the pair of triangular openings being disposed on a first top side of the front sidewall, a second triangular opening of the pair of triangular openings being disposed on a second top side of the front sidewall, the first and second top sides being opposite of one another along the front sidewall.
12. The odor reducing device according to claim 1, wherein
    the bottom opening is a bottom slot.

* * * * *